United States Patent
De Bruijn et al.

(10) Patent No.: US 9,736,402 B2
(45) Date of Patent: Aug. 15, 2017

(54) SYSTEM FOR HYPERSPECTRAL IMAGING IN VISIBLE LIGHT, METHOD FOR RECORDING A HYPERSPECTRAL IMAGE AND DISPLAYING THE HYPERSPECTRAL IMAGE IN VISIBLE LIGHT

(71) Applicant: KONINKLIJKE PHILIPS N.V., Eindhoven (NL)

(72) Inventors: Frederik Jan De Bruijn, Eindhoven (NL); Remco Theodorus Johannes Muijs, Meteren (NL); Jorrit Ernst De Vries, Culemborg (NL); Bernardus Hendrikus Wilhelmus Hendriks, Eindhoven (NL); Drazenko Babic, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/400,200

(22) PCT Filed: Mar. 12, 2014

(86) PCT No.: PCT/IB2014/059652
§ 371 (c)(1),
(2) Date: Nov. 10, 2014

(87) PCT Pub. No.: WO2014/147515
PCT Pub. Date: Sep. 25, 2014

(65) Prior Publication Data
US 2015/0381908 A1 Dec. 31, 2015

Related U.S. Application Data

(60) Provisional application No. 61/803,169, filed on Mar. 19, 2013.

(51) Int. Cl.
*H04N 5/33* (2006.01)
*A61B 6/00* (2006.01)
(Continued)

(52) U.S. Cl.
CPC .......... *H04N 5/332* (2013.01); *A61B 5/0035* (2013.01); *A61B 5/0075* (2013.01);
(Continued)

(58) Field of Classification Search
CPC .......... H04N 5/332; H04N 9/04; H04N 9/646; H04N 9/3194; G02B 3/0006;
(Continued)

(56) References Cited

U.S. PATENT DOCUMENTS

2008/0027317 A1* 1/2008 Wood .................. A61B 5/0059
600/427
2008/0298642 A1* 12/2008 Meenen .................. G06K 9/00
382/115

(Continued)

FOREIGN PATENT DOCUMENTS

| CH | WO/2010/131180 | * 11/2010 | ............... A61B 6/00 |
| EP | 2075616 A1 | 7/2009 | |
| WO | WO2010067281 A1 | 6/2010 | |

OTHER PUBLICATIONS

Arash Taheri et al, "Can Light-Field Photography Ease Focusing on the Scalp and Oral Cavity?", Skin Research and Technology, vol. 19, No. 3, Jan. 20, 2013, pp. 288-290, XP055122134.
(Continued)

*Primary Examiner* — Michael P LaPage
(74) *Attorney, Agent, or Firm* — Larry Liberchuk (57) ABSTRACT

An imaging system comprises a light field camera (3) for recording a hyperspectral light field (CLF). The system also comprises a light projector (4) for projecting a light field in visible light (PLF). The camera and the projector share a
(Continued)

common optical axis. The projector projects a light field (PLF) based on the hyperspectral light field (CLF) captured by the light field camera.

13 Claims, 5 Drawing Sheets (51) Int. Cl.
G01J 5/08 (2006.01)
A61B 5/00 (2006.01)
G01J 3/28 (2006.01)
G01J 5/02 (2006.01)
G02B 3/00 (2006.01)
G02B 27/14 (2006.01)
G06T 5/00 (2006.01)
H04N 9/04 (2006.01)
H04N 9/31 (2006.01)
H04N 9/64 (2006.01)
G01J 5/00 (2006.01)
A61B 90/00 (2016.01)

(52) U.S. Cl.
CPC ............ A61B 5/0077 (2013.01); A61B 5/489 (2013.01); A61B 6/5247 (2013.01); G01J 3/2823 (2013.01); G01J 5/025 (2013.01); G01J 5/0896 (2013.01); G02B 3/0006 (2013.01); G02B 27/141 (2013.01); G06T 5/003 (2013.01); H04N 9/04 (2013.01); H04N 9/3194 (2013.01); H04N 9/646 (2013.01); A61B 6/4441 (2013.01); A61B 2090/374 (2016.02); A61B 2090/378 (2016.02); A61B 2090/3762 (2016.02); G01J 2005/0077 (2013.01); G06T 2207/10024 (2013.01); G06T 2207/10052 (2013.01)

(58) Field of Classification Search
CPC ... G02B 27/141; A61B 5/0075; A61B 5/0077; A61B 5/0035; A61B 2019/5236; A61B 6/5247; G01J 5/0896; G01J 3/2823; G01J 5/025; G06T 2207/10024; G06T 2207/10052
See application file for complete search history.

(56) References Cited

U.S. PATENT DOCUMENTS

| 2009/0015686 | A1 | 1/2009 | Alsberg |
| 2010/0177184 | A1 | 7/2010 | Berryhill |
| 2012/0170824 | A1 | 7/2012 | Hendriks |
| 2012/0200829 | A1 | 8/2012 | Bronstein |
| 2013/0322729 | A1* | 12/2013 | Mestha ................ A61B 5/02 382/134 |

OTHER PUBLICATIONS

Miyake R.K. et al.' "Vein Imaging: A New Method of Near Infrared Imaging Where a Processed Image is Projected Onto the Skin for the Enhancement of Vein Treatment", American Society for Dermatologic Surgery, vol. 32, pp. 1031-1038, 2006.

Levoy M. et al., "Light Field Microscopy", ACM Transactions on Graphics, vol. 25, No. 3, pp. 924-934, Jul. 2006.

Veeraraghavan A. et al., "Dappled Photography: Mask Enhanced Cameras for Heterodyned Light Fields and Coded Aperture Refocusing", ACM Transactions on Graphics (Proc. SIGGRAPH 2007), vol. 26, No. 3, Jul. 2007.

Levin A. et al., "Image and Depth Form a Conventional Camera with a Coded Aperture", ACM Transactions on Graphics (Proc. SIGGRAPH 2007), vol. 26, No. 3, Jul. 2007.

Dowski E.R. et al., "Extended Depth of Field Through Wave-Front Cilding", Applied Optics, vol. 34, No. 11, pp. 1859-1866, Apr. 1995.

Nagahara H. et al., "Flexible Depth of Field Photography", in Proceedings of European Conference on Computer Vision (ECCV), Oct. 2008.

Bishop T.E. et al., "Plenoptic Depth Estimation from Multiple Aliased Views", 2009 IEEE 12th International Conference on Computer Vision Workshops (ICCV Workshops), IEEE, pp. 1622-1629, Los Alamitos, 2009.

Wanner S. et al., "Generating EPI Representations of 4D Light Fields with a Single Lens Focused Plenoptics Camera", Proceedings ISVC 2011, G. Bebis et al. (eds.), pp. 90-101, 2011.

Adelson E.H. et al., "The Plenoptic Function and the Elements of Early Vision", from M. Landy et al (Eds), Computational Models of Visual Processing, pp. 3-20, Cambridge, MA: MIT Press (1991).

Cassinelli A. et al., "Camera-Less Smart Laser Projector", Ishikawa Komuro Laboratory—the University of Tokyo, SIGGRAPH Emerging Technologies, Mar. 23, 2010, www.k2.t.u-tokyo.ac.jp/.../SLP/SLP_LV2010.pdf.

Schmeits H.A.W. et al., "Sweeping Focus Camera", Technical Note PR-TN 2009/00745, Issued: Dec. 2009, Computational Imaging IP Generation, Koninklijke Philips Electronics N.V. 2009.

Vlutters R. et al., "Low-Cost Depth Estimation", Technical Note PR-TN 2009/00622 Issued: Nov. 2009, Computational Imaging Applications, Computational Imaging for Digital Pathology, Computational Imaging IP Generation, Koninklijke Philips Electronics N.V. 2009.

De Bruijn F.J. et al., "Computational Imaging: Opportunities for Consumer Lifestyle and Life Sciences", Technical Note PR-TN 2008/00697 Issued: Nov. 2008, The 2009 Projects on Computational Imaging in the Lifestyle Domain and in the Healthcare Domain, Koninklijke Philips Electronics N.V. 2008.

Vlutters R. et al., "Computational Imaging for Digital Pathology", Technical Note PR-TN 2009/00104 Issued: Feb. 2009, Healthcare Incubator on Digital Pathology, Koninklijke Philips Electronics N.V. 2009.

* cited by examiner

SYSTEM FOR HYPERSPECTRAL IMAGING IN VISIBLE LIGHT, METHOD FOR RECORDING A HYPERSPECTRAL IMAGE AND DISPLAYING THE HYPERSPECTRAL IMAGE IN VISIBLE LIGHT

FIELD OF THE INVENTION

The invention relates to a system for hyperspectral imaging comprising a camera for recording a hyperspectral image of an object and a display device for displaying the recorder hyperspectral image in visible light, and to a method for recording an hyperspectral image and displaying the hyperspectral image in visible light.

BACKGROUND OF THE INVENTION

Hyperspectral imaging is known to reveal details impossible or difficult to see by the human eye, such as for instance tissue differences in a human. In hyperspectral imaging an image is taken of an object in one or more wavelength bands where at least one wavelength band is at least partly invisible to the human eye or at least very difficult to see. This image is then converted into a visible image, which image is provided in visible light to a viewer. Hyperspectral imaging can be based both by spectrally selective illumination (i.e. illumination an object with light in a certain wavelength band) and by spectrally selective filtering prior (i.e. using a filter that transmits only light in a certain wavelength band) to image capture. In both cases image processing is required to generate a resulting image revealing the structure contrast of interest.

In such a system conventionally a hyperspectral image (e.g. image extending beyond the visible spectrum) is taken and the result is shown on a display screen. Sitting behind the display screen the viewer, interested in not or hardly visible details of the object under observation, can study the image on the screen in visible light as it would appear in for instance UV light, or in IR light.

Although using a screen is a very useful technique, the possibilities are limited. It has been proposed to project a hyperspectral image on a studied object, for instance in R. K. Miyake, H. D. Zeman, F. H. Duarte, R. Kikuchi, E. Ramacciotti, G. Lovhoiden, C. Vrancken, "Vein imaging: A new method of near infrared imaging where a processed image is projected onto the skin for the enhancement of vein treatment", *Dermatologic, Surgery*, vol. 32, pp. 1031-1038, 2006. The projection is performed with a laser projector.

It is difficult, if not near impossible, using the known technique to provide a good sharp projection wherein the projection coincides to a relatively high degree of alignment unless the object, in the known prior art the skin, is stationary and to a high degree flat.

It is an object of the invention to provide a system and a method that allows directly seeing hyperspectral details of an object under observation and in correct alignment.

SUMMARY OF THE INVENTION

To this end the system of the invention is characterized in that the system the camera is a light field capturing camera and the display device is a light field projector wherein the camera and projector share a coaxial optical path and wherein the camera is arranged to capture a hyperspectral light field, and comprises an output for sending data on the captured hyperspectral light field to an input of the light field projector and the light field projector is arranged to project a light field in visible light over the object based on the data received from the camera.

To this end the method of the invention is characterized in that a light field in a hyperspectral range of radiation of an object is captured by a light field camera, the data on the light field captured by the camera is processed to provide projection image data for a light field projector, the light field projector projecting a light field based the projection image data over the object, wherein the camera and projector share a coaxial optical path and a light field in visible light is projected on the object by the light field projector.

The light field capturing camera captures a light field in a hyper range of the spectrum, i.e. in a spectral range of radiation at least partly not visible to the human eye and the light field projector projects a light field in visible light. The light field projector forms a display device for displaying the recorder hyperspectral image in visible light. The projected light field causes the display of a projected 3D image overlaying the object, said 3D image being sharp throughout a large range of depths. A shared coaxial optical path provides for a relatively easy alignment of captured and projected light fields. This allows accurate and real time projection by the projector of the hyperspectral image in visible light on the object of observation of which the camera has captured the hyperspectral light field, also in case the object of observation is not flat but has a 3D form.

A light field capturing camera has, compared to a regular 2D or even a 3D camera, the advantage that a complete light field is obtained, with the possibility of obtaining sharp images throughout a range of depths. A normal 2D camera does not provide a large depth of view and although a 3D camera can provide some depth information, neither are capable of providing a sharp image throughout a range of depths. A light field camera is also called a plenoptic camera. A light-field camera is a camera that captures light field information about a scene using plenoptic imaging. Plenoptic imaging captures an incident light field preserving both intensity and direction of incident light. The implementation of a plenoptic imaging system can be based on various techniques: a microlens array as in M. Levoy et al., "Light field microscopy", *ACM Trans. on Graphics*, vol. 25, no. 3, pp. 924-934, July 2006; dappled photography with a continuously graded attenuation mask as in A. Veeraraghavan et al., "Dappled photography: Mask enhanced cameras for heterodyned light fields and coded aperture refocusing", *ACM Trans. on Graphics (Proc. SIGGRAPH* 2007), vol. 26, no. 3, July 2007; aperture encoding mask as in A. Levin et al., "Image and depth form a conventional camera with a coded aperture", *ACM Trans. on Graphics (Proc. SIGGRAPH* 2007), vol. 26, no. 3, July 2007; wavefront encoder as in E. R. Dowski et al., "Extended depth of field through wave-front coding", *Applied Optics*, vol. 34, no. 11, pp. 1859-1866, April 1995; sweeping-focus imaging as in H. Nagahara et al., "Flexible Depth of Field Photography", in *Proc. ECCV* 2008, October 2008. Plenoptic imaging stores spatial information of the incident light field. The captured light field is in fact 4-dimensional, as each light ray is characterized by a 2D location on the sensor and a horizontal and vertical angle of incidence, adding 2 more dimensions. The projected light field creates an image on the object that is sharp throughout a large range of optical depths.

Of the techniques described above using a microlens array is preferred. In a continuously graded attenuation mask and in an aperture encoding mask some of the light passing through the mask is attenuated, leading to a loss in intensity. In a microlens array, a higher percentage of the available light is used.

A microlens array is situated between a lens and an image sensor of the plenoptic camera. The microlens array refocuses light captured by the lens onto the image sensor thereby creating many small images taken from slightly different viewpoints. The 3D information is stored in the small images, each of which is produced by a single microlens. Each of the small images has a relatively low spatial resolution.

Another type of light field capturing camera that does not use a microlens array, is a system that uses a so-called sweeping focus or sweeping lens technique. In such cameras the focusing lens and/or the sensor position is changed during capturing of the image. This technique amounts to integrating images at the sweep of the focus (i.e. in a particular range of depth of fields). The resulting image comprises for the focus sweep all image information and also captures all available light. The image taken can be deconvoluted to provide sharp images at various depths and reconstruct a plenoptic projected light field. Using a microlens array is preferred since the light field can be obtained instantaneously. Using a microlens it is relatively easy to align the captured light field, captured by the camera, and the projected light fields, projected by the projector.

Preferably the camera and the projector share common chain of optical imaging elements along the shared coaxial optical axis. This enables better alignment of the captured light field and the projected light field.

Preferably the system comprises an element providing a plenoptic function being positioned in the shared coaxial optical path.

Providing the element providing a plenoptic function in the shared coaxial path increases the ease of alignment of captured and projected light field.

Such elements may be a microlens array, a coded aperture, wavefront encoder.

Of these elements the microlens array is preferred.

In embodiments the system comprises a beam splitter for splitting light paths from and to the common optical axis to and from the light field camera respectively light field projector the beam splitter having a dichroic, spectrally selective property. The dichroic beam splitter passes or reflects light in the hyperspectral range to the camera, while reflecting or passing light in the visible range coming from the projector.

In another embodiment a spectrally selective illumination is used.

In preferred embodiments the system is a mobile, preferably portable system, for instance a hand held system. This allows e.g. a physician to view veins immediately and on the spot. When needles have to be inserted in a vein such on the spot inspection is a great advantage.

In another preferred embodiment the system is a part of a surgical luminary.

In another embodiment the system is a part of a larger system the larger system further comprising a secondary imaging system for providing secondary image data on an internal image of the object under observation, wherein the system comprises a processor to provide depth information based on the data of the captured hyperspectral light field and means to format, based on the depth information, the secondary data into an image projected on the object. The secondary imaging system may for instance be an X-ray system, MRI, CT, PET-CT or ultrasound system.

BRIEF DESCRIPTION OF THE DRAWINGS

These and other objects and advantageous aspects will become apparent from exemplary embodiments that will be described using the following Figs.

The figures are not drawn to scale. Generally, identical components are denoted by the same reference numerals in the figures.

DETAILED DESCRIPTION OF PREFERRED EMBODIMENTS

It is an object of the invention to provide a result image as projection on the observed tissue, yet in such a way that the projection is always in correct focus on tissue, regardless the surface curvature of the tissue or its orientation with respect to the capturing/projecting device.

Hyperspectral imaging provides contrast, e.g. tissue contrast that is invisible by the naked eye. The improved contrast can for instance be used to reveal blood vessels and nerves during surgery or introduction of needles into veins. It can also be used to identify malignant tissue.

Hyperspectral image capture can be based on a monochrome, non-spectral-selective image sensor and the use of spectrally selective filtering prior to the image sensor, similar to an normal RGB camera but with more color channels and with different filter characteristics. Otherwise, hyperspectral image capture can also be based on spectrally selective (controlled) illumination in combination with an unfiltered image sensor. A combination of 'filtered illumination' and 'filtered acquisition' is also possible.

Differences in spectral response between different materials is generally converted into a visible contrast (b/w or pseudo-color) by way of a linear weighted combination of different spectral input values for the same spatial location. Various different predetermined weight combinations lead to different tissue contrasts. As such, the result from hyperspectral image capture is generally an image with an enhanced contrast of the material (liquid or tissue) of interest. This way, e.g. it is possible to reveal the position of veins and arteries on the basis of their subtle but distinct spectral response compared to e.g. the skin. The corresponding result image depicts the blood vessel structure directly under the observed skin area. It is an object of the invention to project the result image in real time on the observed tissue, in real time and in constant correct alignment with the observed tissue.

Disadvantage of current hyperspectral imaging systems in general is that the result data appears separately on a display screen, such that the geometrical relation with the real tissue is easily lost. Nowadays, the use of augmented reality glasses is a popular method to keep the result data, generated in the glasses, which form the display screens, in constant alignment with a tissue that is observed by the surgeon. A major disadvantage is that this requires a head-mounted device of which the location and orientation is tracked against the position of the working area, adding to the complexity of such solutions. Moreover, it forces the specialist to wear special glasses. Also, in operating theatres many people are present; if only the specialist carries special glasses assistants are not able to see what the specialist is seeing, unless they also wear glasses and the position and orientation of said glasses is also tracked, adding immense complexity to the system.

It is an object of the invention to provide a system and a method allowing directly seeing hyperspectral details of an object under observation and in correct alignment without the need for 3D object-tracking or wearing special glasses.

Figure 1:
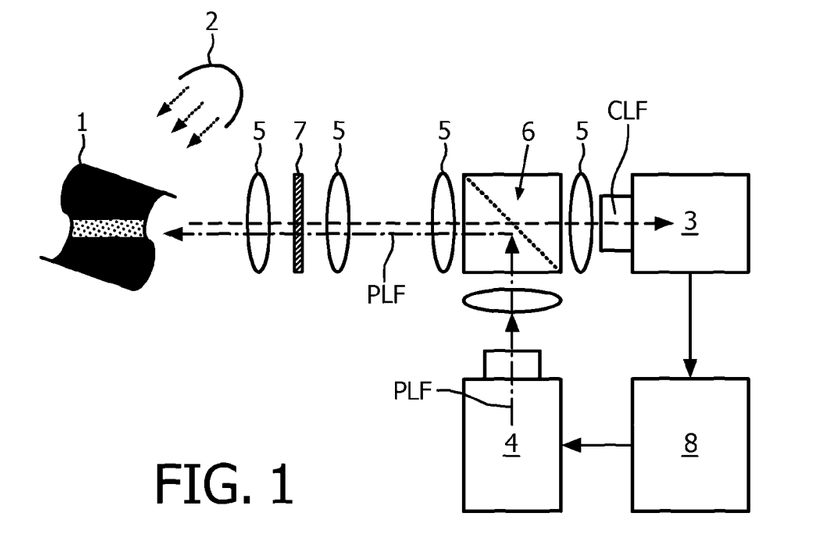
FIG. 1 illustrates an embodiment of a system according to the invention.

FIG. 1 illustrates an embodiment of a system and method according to the invention.

On object 1, in this example a human tissue, hyperspectral light is shone from hyperspectral source 2. The light source may be part of the system, and in preferred embodiments it is, or could be separately provided. The hyperspectral source causes the issue to form a hyperspectral image, for instance in IR or in UV. Alternatively the object may itself, independent from the presence of a hyperspectral light source, provide a hyperspectral image, i.e. an image in a wavelength not or difficult to see with the human eye. For instance, the object may be provided with a substance that, after having been illuminated in the past, phosphoresces in a particular wavelength.

Alternatively or in addition the tissue 1 may, even without a light source being shone upon it, provide an IR image showing details in an IR wavelength that are invisible in visible wavelengths. Alternatively or in addition, the object may be illuminated with a source that supplies visible light as well as for instance UV and/or IR light a wavelength selective element is provided in the light path to the camera or in the camera so that the camera records the hyperspectral image.

Alternatively or in addition, the camera may be provided with sensor pixels that electronically record the image in visible light and sensor pixels that record the image in a hyperspectral range of radiation and the data from the hyperspectral sensitive pixels is used for the hyperspectral light field.

It is also possible to use a light field camera that comprises pixels that are sensitive both to visible light and to the hyperspectral (for instance IR and/or UV part of the spectrum) radiation and time-sequentially put a wavelength selective filters in front of a source providing visible light as well hyperspectral radiation, wherein the filters pass either visible light or a hyperspectral part of the spectrum and synchronize the data acquisition from the light field camera with the time-sequential illumination to provide the light field data in the hyperspectral range and possibly also in the visible part of the spectrum.

In embodiments the hyperspectral image is taken in a UV or IR range of the electromagnetic spectrum. These embodiments are preferred.

However, the hyperspectral image may be taken in other ranges of the electromagnetic spectrum, for instance by means of X-ray imaging or Terahertz imaging.

For such embodiments the light field camera is an X-ray or Terahertz imaging device providing light field data in the X-ray or Terahertz part of the electromagnetic spectrum.

The 4D light field provided by the tissue is captured by light field camera 3 through a lens system 5. The lens system 5 comprises a beam splitter 6 and a microlens array 7. The captured light field is denoted by CLF in FIG. 1. The light field camera comprises a sensor on which the light field is captured. The data on the captured light field are provided, via an image processor 8, to a light field projector 4. The output of the camera thus provides data for the input of the projector. "Providing data" should, however, not be interpreted as to mean that the camera data are directly supplied to the projector, but that the camera data form a basis for the data for the projector. Processing of the data may be provided in between the output of the light field camera 3 and the input of the light field projector 4. The light field projector projects a light field PLF on the tissue 1 via beam splitter 6 and microlens array 7. It is preferred that the light source forms part of the system. This enables a control of the intensity of the light shining on the object 1. The embodiment of FIG. 1 shows a system wherein a hyperspectral image is taken in UV or IR. As explained above in various ways such an image can be taken. For simplicity sake the in the figure no wavelength selective element has been shown. Such a wavelength selective element can be for instance put in front of the source, or in front of the camera or, if the camera comprises different pixels for visible light than for UV or IR, the data can be electronic filtered, i.e. by means of a data filter to filter the data acquired by the light field camera.

Due to the generally short focal length of the microlenses in the microlens array, the microlens array tends to create an array of micro images also focused very closely behind the lens array. The optical lens system between microlens array 7 and beam splitter 6, and also behind the beam splitter relays this (micro-)image plane such that the micro image plane coincides with the sensor plane of the camera and with the plane of the image-generating element in the projector. The image generating element can be for instance an array of light emitting elements, and array of switching mirrors (typ. a DLP element), or an array of LCD light shutters.

The projector 4 and the camera 3 share a common coaxial optical axis. A common optical axis is illustrated in FIG. 1 by the fact that the light rays are parallel. The advantage of using a common optical path for image capture and projection is that the projected overlay is in good alignment with the associated tissue. Apart from scaling for differences in sensing- and projecting-element size, no complex 3D processing is required.

Each microlens can be regarded as a super-pixel that not only stores angular information in addition to the intensity of the incident light at the location of that 'super-pixel'. Similarly, a projector that generates the same micro-images in association with a microlens array will lead to a projection of which the focal plane coincides with the original surface plane, regardless its curved shape. The use of a common optical path and alignment of sensor and projector pixels will lead to a projection that is always in focus on the surface that is captured with the camera. The use of a microlens array is preferred since a microlens array does not attenuate the light field.

The system can be called a plenoptic hyperspectral augmented-reality system providing range-invariant capture and projection.

Depending on the application, the beam splitter 6 can also provide spectral selectivity. Particularly when the image capture is primarily in an invisible light domain such as IR, the beam splitter can have a dichroic property. In that case, the incident IR light follows a straight path towards the camera, and the visible light from the projector is refracted by the beam splitter.

Figure 2:
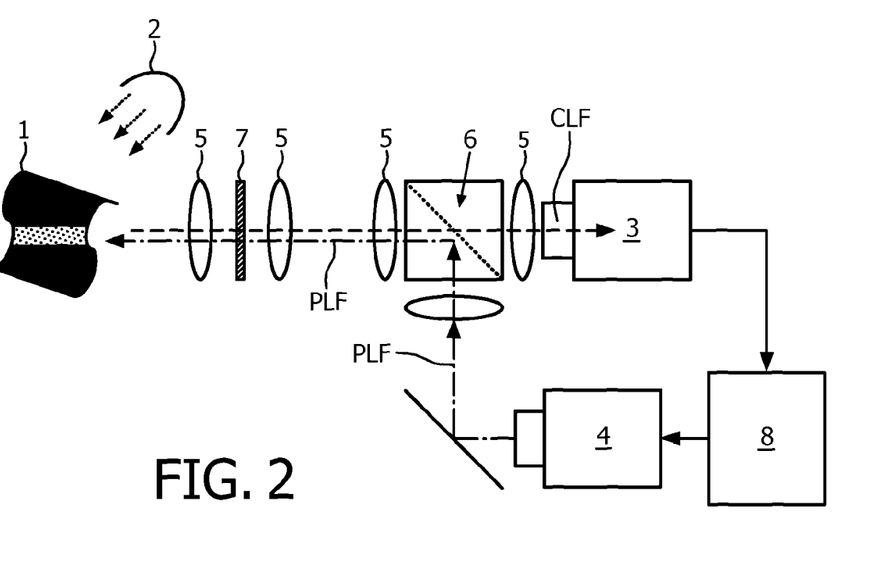
FIG. 2 illustrates another embodiment of a system according to the invention.

FIG. 2 illustrates also an embodiment of a system according to the invention. A mirror is used to fold the projected light field. This allows in circumstances a more compact design of the system.

Figure 3:
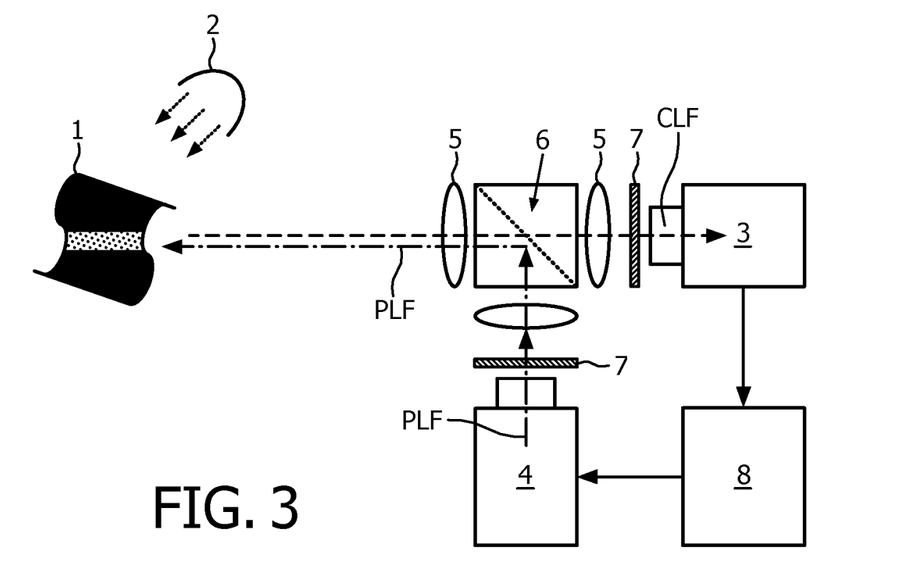
FIG. 3 illustrates another embodiment of a system according to the invention.

FIG. 3 illustrates a further embodiment. In this embodiment the camera and the projector comprise different microlens arrays. The systems of FIGS. 1 and 2 are preferred but, if for instance the spectral wavelength of the hyperspectral imaging requires a specific material for the microlens that is less suitable for visible light wavelength, separate microlens arrays can be used. In the FIGS. 1 to 3 the camera and the projector share common imaging elements along the common optical axis.

Figure 4:
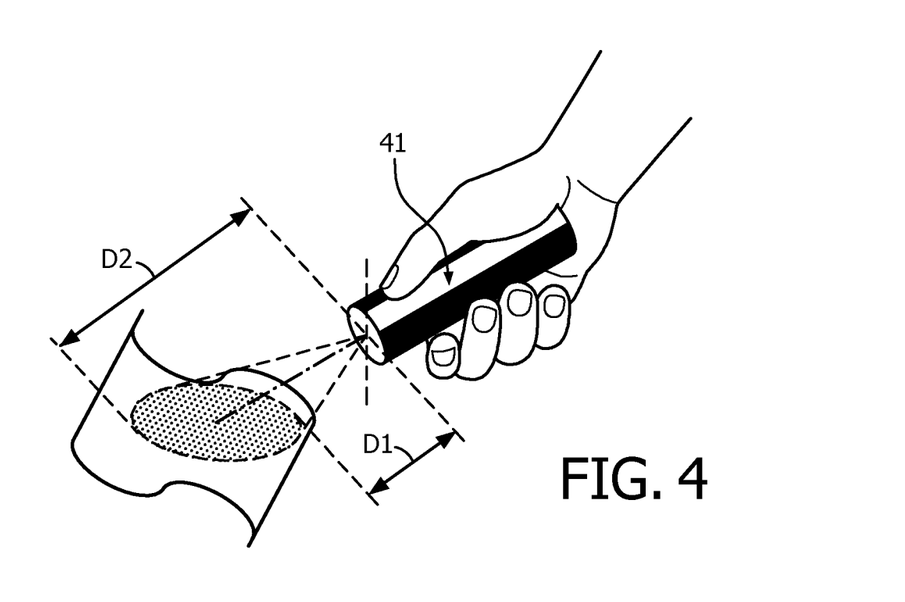
FIG. 4 illustrates a hand-held device comprising a system according to the invention.
Figure 5:
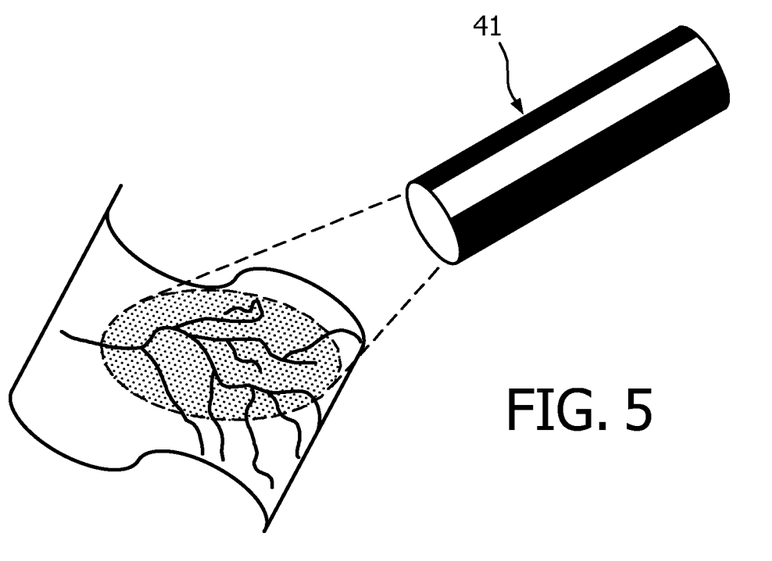
FIG. 5 illustrates vein image enhancement using a hand-held system as shown in FIG. 4.

FIGS. 4 and 5 illustrates a preferred embodiment of the system. In this embodiment the system is a mobile, preferably portable system. In this embodiment the system is a hand held system. The system comprises a hyperspectral source within the hand held device and a camera and projector, wherein the portable device is used to capture tissue region and provide a projection of otherwise invisible data, e.g. on the position of veins, as illustrated in FIG. 5. Having a properly image capture and properly projected sharp image of e.g. veins using a portable device provides great advantages in situation wherein it is important or even vital to find a vein fast. When inserting a needle in a vein in e.g. an emergency situation, such as an accident, it may be critical or even a matter of life or death to work fast and accurately and to need only a relatively simple device which can be operated easily and brought to the emergency situation. Existing systems do not provide the possibility to, accurately and in real time, and on the spot of the accident, provide an image of the position of veins or other hyperspectral details. The portable system of FIGS. 4 and 5 does provide this possibility. In this case example the system is hand held. The system may be worn on a helmet or on a sleeve so that the hands are free to insert a needle or perform other medical procedures.

Figure 6:
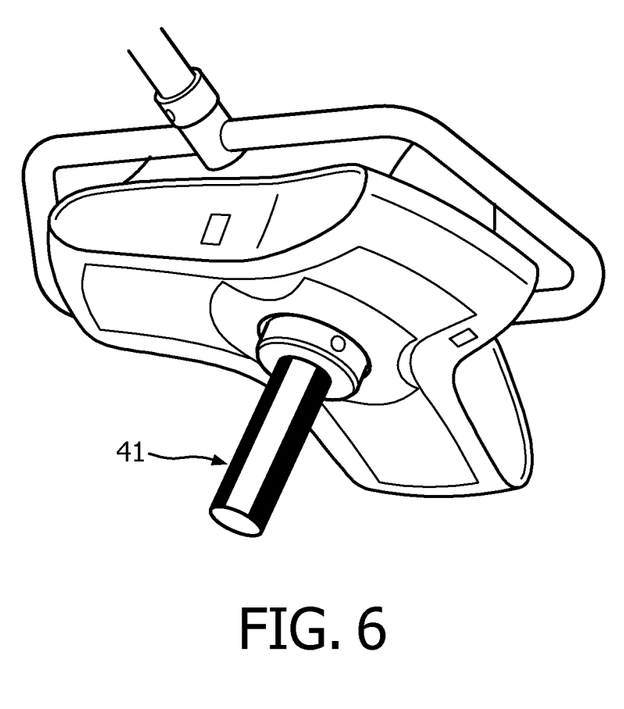
FIG. 6 illustrates a surgical or dentist lamp comprising a system according to the invention.

FIG. 6 illustrates use of a system according to the invention in a surgical lamp or a dentist lamp. The lamp can optionally provide spectrally selective illumination as part of the hyperspectral image capturing.

In yet another embodiment, the invention may be incorporated in a system comprising a secondary imaging system, for instance X-ray imaging system, or more generally in a system that produces an internal image of the object under observation, e.g. a system as described in patent application WO2010067281.

Figure 7:
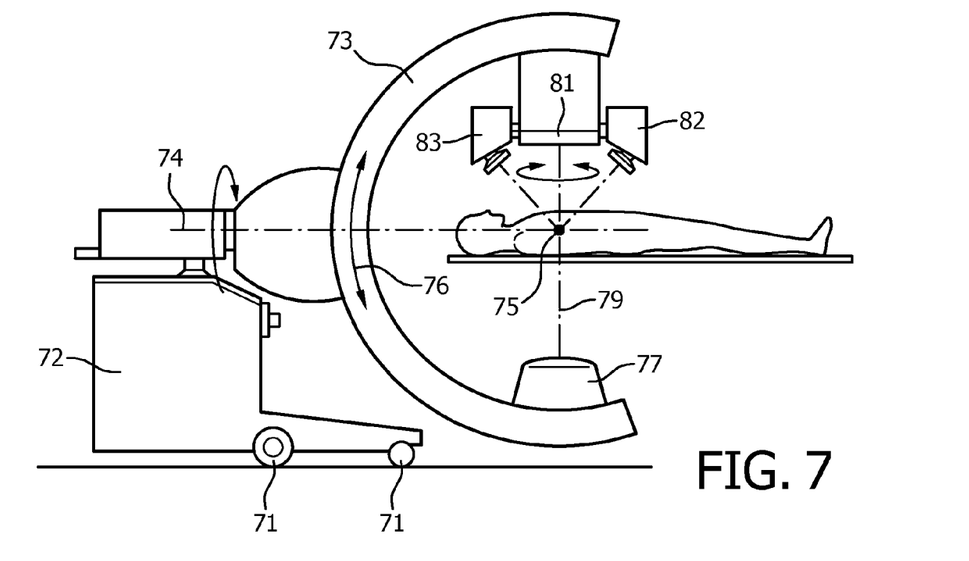
FIGS. 7 and 8 illustrate an X-ray system comprising a system according to the invention.

In FIG. 7 a schematic drawing of a system for such an embodiment is shown.

The system comprises an X-ray C-arm with two cameras sensitive to UV, Visible, or Infrared wavelengths attached. The illustrated C-arm X-ray system is composed of a base frame 72 movable on wheels 71 and at which a C-arm 73 is seated such that it is rotatable around the axis 74 (angulation) such that it also can be turned around an axis 75 in the direction of the double arrow 76 (orbital rotation). Although a mobile system is described here, the X-ray system can also be fixed to the wall as in a cathlab. An X-ray source 77 and a detector 81, preferably a rectangular flat detector, residing 180 degree opposite one another, are secured to the C-arm 73 in the region of its ends.

The X-ray C-arm is capable of acquiring a three-dimensional internal image of the patient. Camera system 82 is attached aside to the detector 81 and is capable of capturing images of the patient's operation field. In a particular embodiment the camera system is capable of three-dimensional imaging of the patient. Furthermore, a hyperspectral imaging system 83 according to the invention is also attached to the detector 81 and is capable of projecting information in visible light back onto the patient in such a way that the images are in focus on the curved surfaces of the patient. For instance structures such as tumour boundaries are better delineated in the hyperspectral image and can be projected back onto the patient in the visible light according to the invention. This makes the tumour boundaries better visible to the surgeon. Apart from this hyperspectral imaging back projection, the back projection of images taken by the X-ray system and converted to visible images is possible by the system 83. For instance, the position of the tumour deep inside the body visible with X-ray imaging is projected back onto the patient body. In this way, the surgeon has a much better indication where the tumour is located. Also, important structures such as large blood vessels that lie just below the surface and are not visible by the eyes can be indicated. In this way, the surgeon knows in advance to be careful when making incisions at this position. Instead of an X-ray system a similar approach can also be applied to a MRI, CT, PET-CT or Ultrasound system. A teraherz imaging system can also be used. All these system provide an internal image of an object under observation and in all cases the data sources produce a stream 2D images which form a secondary data set in addition to the data based on the camera acquisitions.

In the system of FIG. 7 the relative positions of the hyperspectral imaging system and the secondary imaging system (the X-ray system in FIG. 7) are known and fixed. This enables a relatively simple matching of hyperspectral and internal imaging.

In systems wherein the relative position of hyperspectral imaging system and secondary internal imaging system are to a more or less greater extent variable preferably means are provided to determine the relative positions of the hyperspectral imaging and the secondary imaging system. This may be done automatically, for instance by providing an electronic means to measure the X, Y and Z coordinates of both imaging systems and preferably also the orientation or axes of the imaging system if this information is relevant. This may of course also be done by a manual input of such data. Alternatively or in addition image features, either naturally occurring or specifically placed within the range of the respective images present in both the hyperspectral and the secondary image may be used to align the hyperspectral and secondary images. For instance small metal objects on the patient at various points which would show in the hyperspectral as well as visible as well as X-ray images could be used for this purpose.

Figure 8:
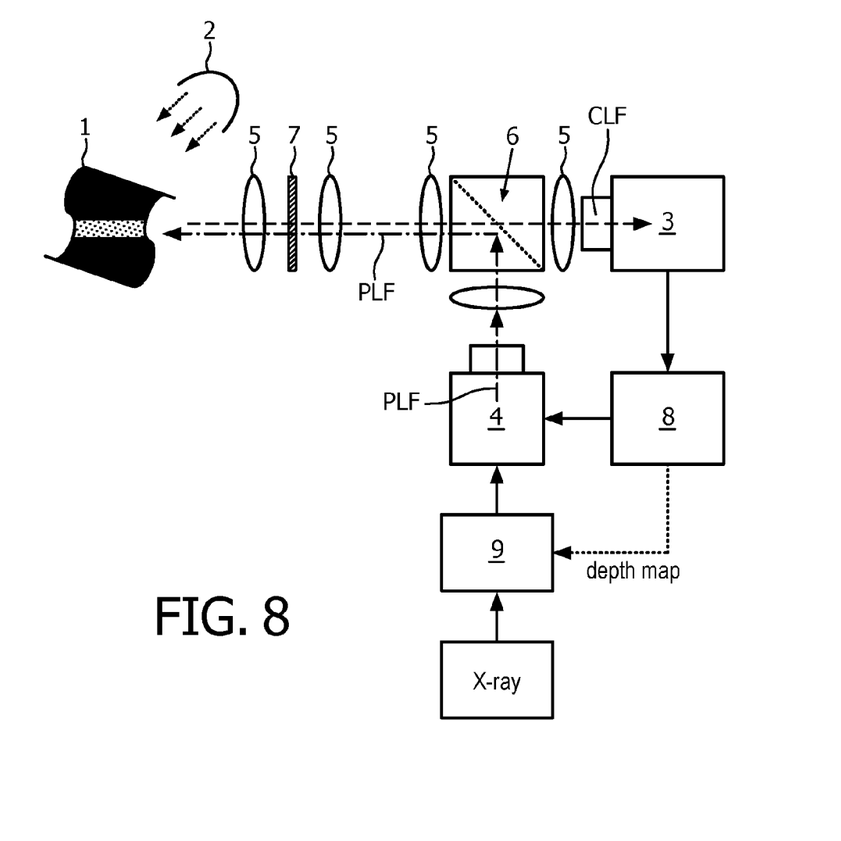

FIG. 8 illustrates the system of FIG. 7 further. The use of such secondary image data coming from for instance the X-ray data requires the explicit calculation of a depth map $d(x,y)$ describing the distance d between the plenoptic camera/projector and the tissue surface for every pixel $(x,y)$ of the projector. This, in contrast to the plenoptic camera data itself which only requires a spatial interpolation to match the input pixel grid of the plenoptic camera to the projector's output pixel grid.

The captured light field comprises depth information. To recover the distance-profile from the captured light-field data, various solutions have been proposed, e.g., by Bishop et al. in T. Bishop, P. Favaro, "Plenoptic depth estimation from multiple aliased views", in: 2009 IEEE 12th International Conference on Computer Vision Workshops (ICCV Workshops), IEEE, pp. 1622-1629, Los Alamitos, 2009 and by Wanner et al. in S. Wanner, J. Fehr, B. Jaehne, "Generation EPI representations of 4D light fields with a single lens focused plenoptics camera", in: Proc. ISVC 2011, G. Bebis et al. eds., pp. 90-101, 2011. This then becomes an extra task that is performed by the processing block 8 in FIG. 8. The recovered depth map d(x,y) is then used in part 9 to reformat the image from the secondary data source into an array of micro-images. In case of proper alignment with the microlens array, also the secondary data will then project in proper focus on the tissue surface, regardless its shape and orientation. Although not shown the part 9 may also have an input for inputting data on the relative positions and/or orientations of the hyperspectral and X-ray imaging system.

Figure 9A:
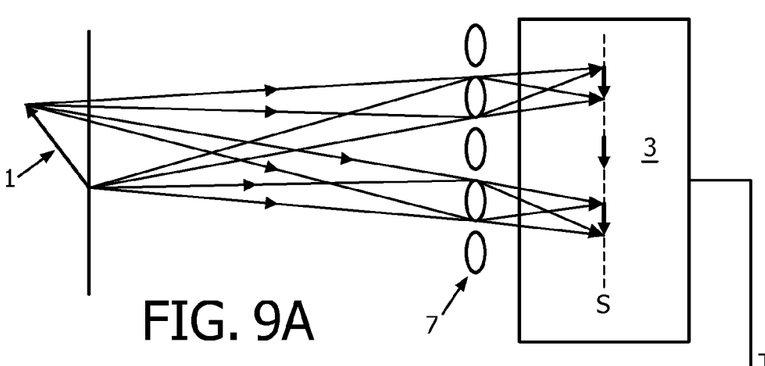
FIG. 9 illustrates the principle of using a micro lens to capture a light field and project a light field.
Figure 9B:
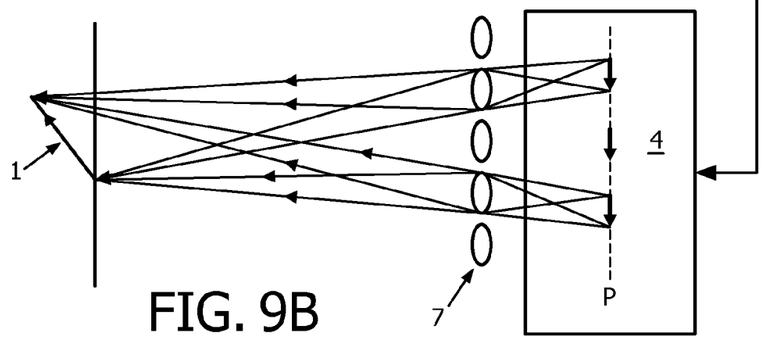

FIG. 9 illustrates the principle of using a micro lens to capture a light field and project a light field. The top part of FIG. 9 illustrates capturing of a light field. Plenoptic imaging stores spatial information of the incident light field. In case a microlens array is used, the 3D information is stored in small micro-images, each of which is produced by a single microlens of the microlens array. The captured light field is in fact 4-dimensional, as each light ray is characterized by a 2D location on the sensor and a horizontal and vertical angle of incidence, adding 2 more dimensions.

Each microlens can be regarded as a super-pixel that not only stores angular information but also the intensity of the incident light at the location of that 'super-pixel'.

The bottom part of FIG. 9 illustrates projecting a light field from pixel of projector 4. The light rays are reversed. A projector that generates the same micro-images in association with a microlens array will lead to a projection of which the focal plane coincides with the original surface plane, regardless its curved shape. The use of a common optical path and alignment of sensor and projector pixels will lead to a projection that is always in focus on the surface that is captured with the camera. If all elements are exactly the same, same size, same position etc. there is a simple one-to-one relation between the pixel of the camera and the pixel of the projector. In reality the two may differ in size or exact location. However, the relation remains simple task of translating (T) and scaling (S). This is performed in processor 8.

The task of translating could also be done mechanically by providing the projector or the camera with a means for translating the sensor or projecting surface in x and y-direction.

Having common optical elements, and in particular a common element that provides the plenoptic function, in FIG. 9 the microlens array 7 increases the correspondence between the optical paths of image recording and projection thereby simplifying the processing.

Figure 10:
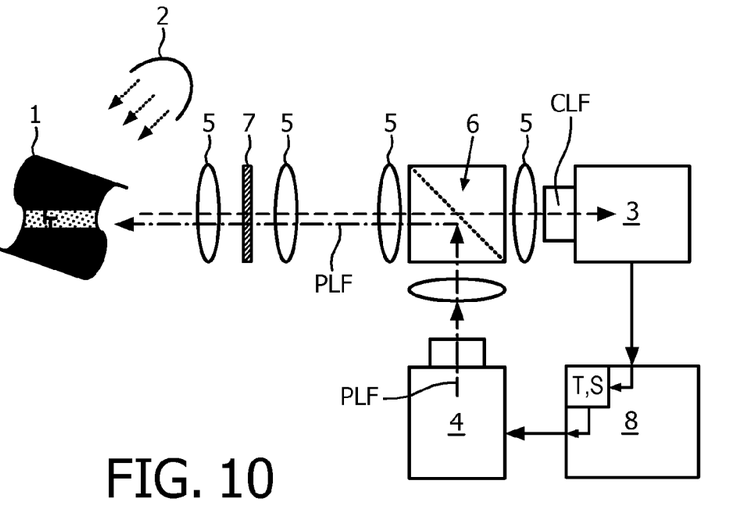
FIG. 10 illustrates a method for fine tuning correspondence between captured and projected light field.

FIG. 10 illustrates a method for finding the required translation and scaling factors.

In FIG. 10 a test image T is provided, this test image T is recorded by the camera 3 which sends the data on the recorded image to processor 8; the processor 8 applies an initial T and S transformation, found for instance by a previous computer generated optical ray tracing assuming known features of camera and projector, to the data and sends it to projector 4. The projected image is compared to the test image, which can for instance be done with a separate camera capable of recording both the hyperspectral image and the projected image. If the test image and the projected image coincide the preset values for T and S are used, if not the values of T and S are varied until the test image and the projected image coincide. This is one way of finding the T and S values. In the FIG. 10 a method for aligning the light field camera and light field projector for a system according to the invention is shown by adjusting the translation and scaling factors T and S to align a test image T to a projected light field image. This testing and alignment procedure is done in preferred methods according to the invention prior to acquiring light field images and projecting light field images.

Summarizing the invention can be shortly described as follows:

An imaging system comprises a light field camera (3) for recording a hyperspectral light field (CLF). The system also comprises a light projector (4) for projecting a light field in visible light (PLF). The camera and the projector share a common optical axis. The projector projects a light field (PLF) based on the hyperspectral light field (CLF) captured by the light field camera.

The invention is not restricted by or to the exemplary embodiments shown in the figures or described above. It will be clear to a person skilled in the art that many variations are possible.

The word "comprising" does not exclude the presence of other elements or steps than those listed in a claim. Use of the article "a" or "a" preceding an element does not exclude the presence of a plurality of such elements.

The word "means" comprises any means, whether in the form of software, hardware any combination thereof for performing the function indicated.

The different elements of a system may be and preferably are in a single device but various elements may be at various physical positions, for instance when light field data are sent from the light field camera to part 8 to be processed to provide projection light field data for projector 4. This part 8 may be in the same device as the camera and the projector, and preferably is, but can also be in a CPU or on a site on the internet or shared by various systems. The data can be transmitted from camera 3 to part 8 by any means for transmission of data, by wire as well as wireless. The same holds for data from part 8 to the projector 4.

The invention also relates, for those embodiments in which the invention is done by means of software, in total or in part, to a computer program product comprising program code means stored on a computer readable medium for performing a method according to the invention and to a computer program product to be loaded by a computer arrangement, comprising instructions for a method according to the invention.

The invention claimed is:

1. An imaging system, comprising:
   a light field capturing camera configured to record an image of an object in a spectral range of radiation from Terahertz through X-ray; and
   a display device configured to display the recorded image in visible light, wherein the display device includes a light field projector, wherein the light field capturing camera and the light field projector share a coaxial optical path and wherein the light field capturing camera comprises an output for sending data on the captured light field to an input of the light field projector, and the light field projector is configured to project a light field in visible light over the object based on the data received from the light field capturing camera; and the system further comprising:

a secondary imaging system configured to provide secondary image data on an internal image of the object under observation, and a processor configured to provide a depth information map describing a distance between a pixel of the light field projector and a surface of the object, based on data on the light field captured by the light field capturing camera and to format, based on the depth information map, the secondary data into an image projected on the surface of the object.

2. The system as claimed in claim 1, wherein the light field capturing camera and the light field projector share a common chain of optical imaging elements along the shared coaxial optical axis.

3. The system as claimed in claim 1, further comprising a microlens array, a coded aperture or a wavefront encoder configured to provide a plenoptic function, and to be positioned in the shared coaxial optical path.

4. The system as claimed in claim 1, further comprising a microlens array configured to provide a plenoptic function.

5. The system as claimed in claim 4, wherein the microlens array is an element common to the light field capturing camera and the light field projector.

6. The system as claimed in claim 1, further comprising a beam splitter configured to split light paths, the beam splitter having a dichroic, spectrally selective property.

7. The system as claimed in claim 1, wherein the imaging system is mobile and portable.

8. The system as claimed in claim 1, wherein the light field capturing camera records the light field in an IR or UV part of the electromagnetic spectrum.

9. The system as claimed in claim 1, wherein the secondary imaging system is an X-ray imaging system, a MRI, CT, PET-CT or Ultrasound imaging system.

10. A method for recording an image of an object in a spectral range of radiation from Terahertz through X-ray and displaying the image in visible light, comprising:

capturing a light field in the spectral range of radiation from Terahertz through X-ray by a light field capturing camera such that the image of the object is obtained, processing the data on the light field captured by the light field capturing camera to provide projection image data for a light field projector, projecting by the light field projector a light field based on the projection image data over the object, wherein the light field capturing camera and the projector share a coaxial optical path, and a light field in visible light is projected on the object by the light field projector;

wherein the data on the light field captured by the light field capturing camera is processed to provide a depth information map describing a distance between a pixel of the light field projector and a surface of the object, and wherein secondary image data is provided on an internal image of the object, and wherein said secondary image data is reformatted using the depth information map, and said reformatted data is provided to the light field projector for projecting on the surface of the object.

11. The method as claimed in claim 10, wherein the light field is captured in an IR or UV part of the electromagnetic spectrum.

12. The method as claimed in claim 10, wherein the secondary image data is provided by an X-ray imaging system, a MRI, CT, PET-CT or Ultrasound system.

13. A non-transitory computer readable storage medium containing a program which causes a computer to:

record an image of an object in a spectral range of radiation from Terahertz through X-ray and display the image in visible light by:

capturing a light field in the range of radiation at least partly not visible to the human eye by a light field capturing camera such that the image of the object is obtained;

processing the data on the light field captured by the light field capturing camera to provide projection image data for a light field projector; and projecting by the light field projector a light field based on the projection image data over the object, wherein the light field capturing camera and the projector share a coaxial optical path, and a light field in visible light is projected on the object by the light field projector;

wherein the data on the light field captured by the light field capturing camera is processed to provide a depth information map describing a distance between a pixel of the light field projector and a surface of the object, and wherein secondary image data is provided on an internal image of the object, and wherein said secondary image data is reformatted using the depth information, and said reformatted data is provided to the light field projector for projecting on the surface of the object.

* * * * *